Figure 1A:
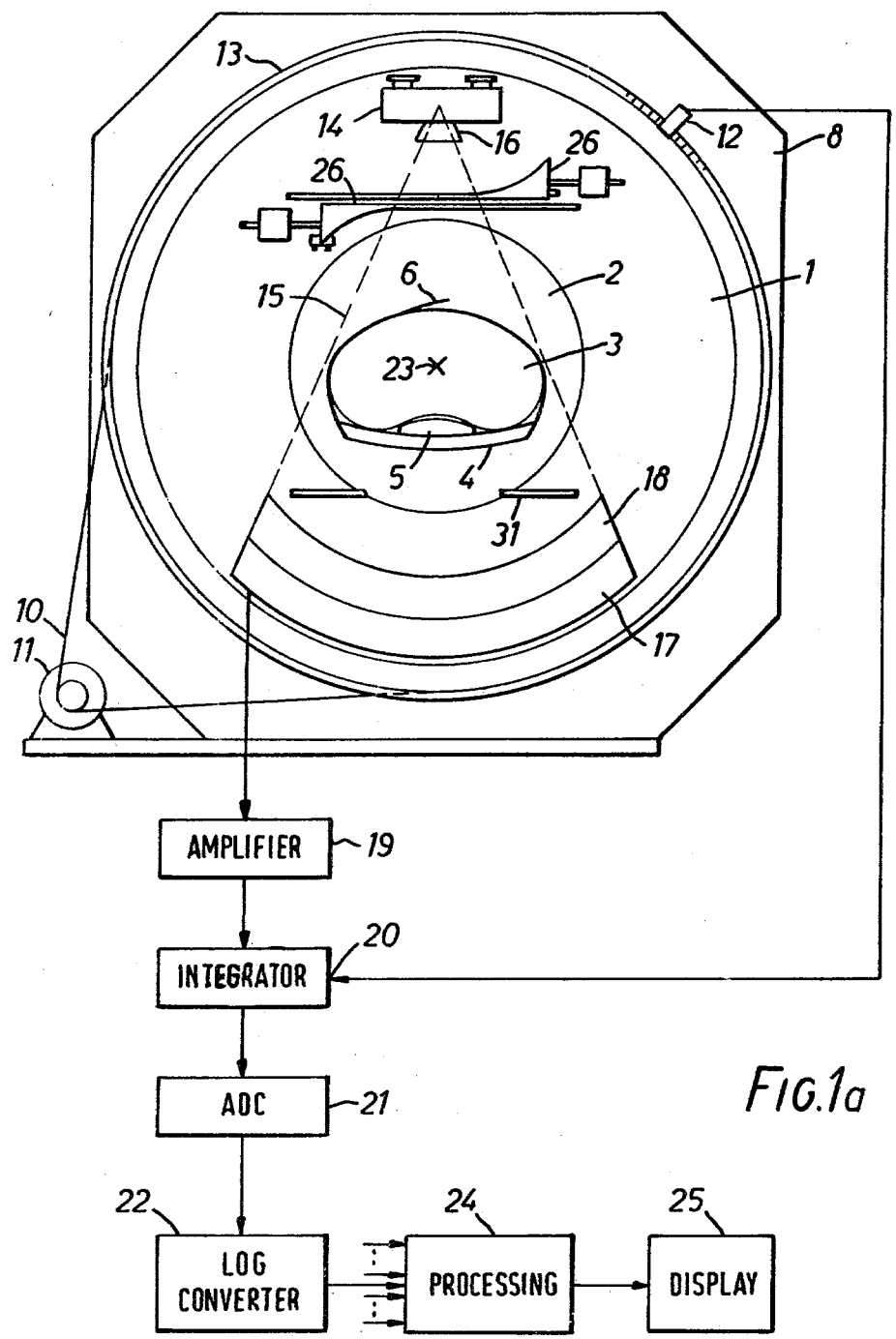

United States Patent [19]

Moore

[11] 4,181,858

[45] Jan. 1, 1980

[54] ADJUSTABLE COMPENSATING DEVICE FOR RADIOGRAPHIC APPARATUS

[75] Inventor: John F. Moore, Lake Bluff, Ill.

[73] Assignee: EMI Limited, Hayes, England

[21] Appl. No.: 865,878

[22] Filed: Dec. 30, 1977

[51] Int. Cl.² ............................................. G03B 41/16
[52] U.S. Cl. ................................. 250/445 T; 250/510
[58] Field of Search .................. 250/445 T, 505, 510, 250/511

[56] References Cited

U.S. PATENT DOCUMENTS

| 2,225,940 | 12/1940 | Grossmann | 250/510 |
|---|---|---|---|
| 3,717,768 | 2/1973 | Edholm | 250/510 |
| 3,755,672 | 8/1973 | Edholm | 250/510 |
| 3,778,614 | 12/1973 | Hounsfield | 250/445 T |
| 3,946,234 | 3/1976 | Hounsfield | 250/445 T |

*Primary Examiner*—Craig E. Church
*Attorney, Agent, or Firm*—Cooper, Dunham, Clark, Griffin & Moran

[57] ABSTRACT

In computerized tomography (CT) apparatus it is usual to rotate a source of radiation about a body which, with associated support, is approximately circular in cross-section. Compensation, for unequal radiation paths through such a circular cross-section body, can be compensated by suitably shaped attenuating masses. This invention provides such masses which are relatively movable, in response to an optical detector system, to adjust for different body sizes. Each mass extends right across the radiation spread so that no discontinuities a rise for particular relative positions of the two masses.

18 Claims, 11 Drawing Figures

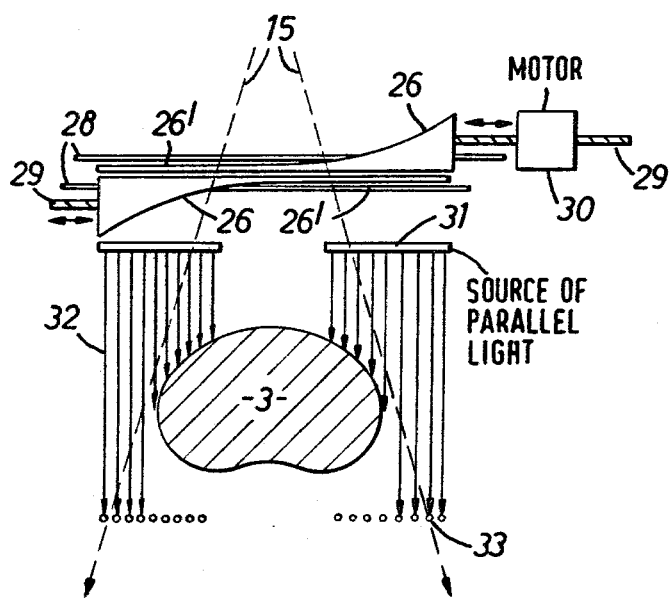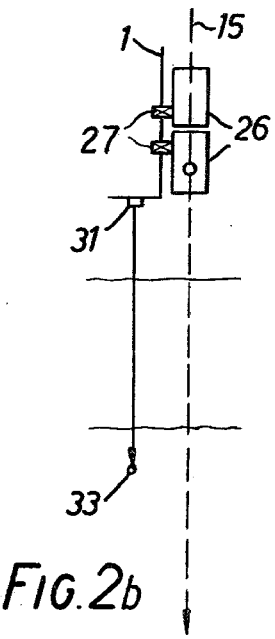
FIG.2a  FIG.2b
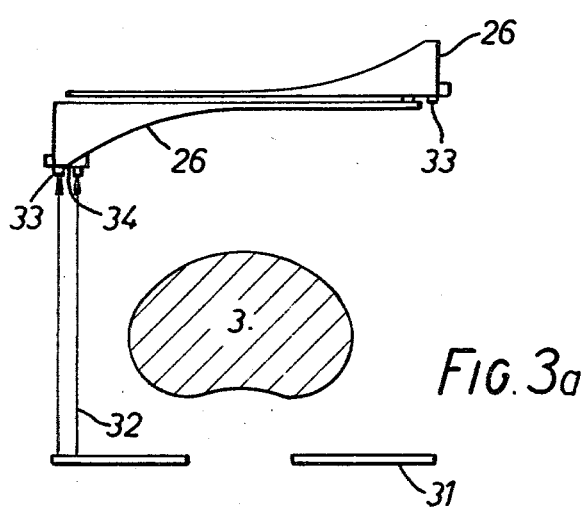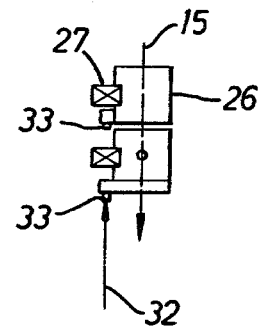
FIG.3a  FIG.3b

ADJUSTABLE COMPENSATING DEVICE FOR RADIOGRAPHIC APPARATUS

The present invention relates to arrangements for use with radiographic apparatus to compensate for variations in the path length of examining radiation through the body of a patient.

A technique, for examining a cross-sectional slice of a patient's body, known as computerised tomographic (CT) scanning is described in U.S. Pat. No. 3,778,614. In U.S. Pat. No. 3,946,234 there is described a CT apparatus which includes a source of fan-shaped spread of radiation in the plane of the slice and an array of detectors arranged to measure the intensity of the radiation after passage through the patient's body. To direct the radiation through the body along a sufficient number of paths in different directions, the source and detectors are reciprocated in the plane of the slice and orbited about a common axis normal to that plane. Output signals from the detectors are processed by any suitable method, such as the convolution method described in U.S. Pat. No. 3,924,129 to provide a representation of the examined slice. The body is of approximately circular cross-section which, in all of these forms of CT apparatus, would lead to the radiation paths through different parts of the body being of different length if not corrected. Forms of compensation, for unequal path length, have been provided by suitably shaped attenuating bodies inserted in the path of the radiation on one or both sides of the body, and such bodies are described, for example, in U.S. Pat. No. 3,946,234.

Further developments of CT scanners have been described, such as that of U.S. Pat. No. 3,881,110 in which examination is effected solely by rotating the fan-shaped spread of radiation about the axis; the radiation can then be measured by detectors which orbit with the fan or else by a stationary array of detectors of sufficient extent to intercept the fan of radiation throughout its orbit. The said attenuating bodies can be adapted to these other forms of apparatus.

In practice attenuating bodies which are suitable for one patient may not be suitable for a patient of a different size. It has therefore been usual to provide different sized bodies and to change them to suit different patients. This is, however, a time-consuming procedure.

U.S. Pat. No. 3,717,768 discloses the use of absorption filters, for conventional radiographic apparatus, in the form of wedge shaped attenuating bodies. The patent shows how light may be projected past the filters, or reflected on the underside thereof, to illuminate the patient's body and thus indicate if the filters are correctly placed. It is proposed that, after visual inspection of the light projected on the patient, the operator should move the filters until the projected pattern is satisfactory.

Another arrangement of such compensating filters is disclosed in U.S. Pat. No. 3,755,672. In one embodiment two wedge-shaped filters are moved into and out of the path of the radiation in response to the intensity of radiation measured by detectors disposed on the other side of the patient. The filters are moved by motors servoed to those detectors and are effective to approximately equalise the total radiation density throughout the body scanned. This scheme is suitable for conventional radiography but has several disadvantages of CT scanning. The adjustment can only be made while the body is being irradiated, which is undesirable. Furthermore the separate, wedge-shaped, attenuating bodies used each intercept only a part of the radiation, at the side of the body. Thus the finite charge of absorption at the end of each wedge leads to a discontinuity, in X-ray absorption, which affects rays passing through the patient's body and hence the finally derived picture.

It is an object of this invention to provide an attenuating arrangement suitable particularly for CT scanning.

It is another object of the invention to provide apparatus, for examining a body by means of penetrating radiation, including: source means for irradiating the body with a fan-shaped distribution of radiation projected in a mean direction; means for scanning the source around the body so as to project the radiation through a cross-sectional slice thereof from a plurality of mean directions; detector means, including a plurality of detectors, for detecting the intensity of radiation transmitted through the body along a plurality of beams within said distribution at each of said mean directions, and means co-operating with said detectors to provide beam data signals indicative of the absorption suffered by said beams in passing through said body for processing to provide a representation of the distribution of absorption of the radiation in said slice; attenuating means, disposed in the path of the radiation, for reducing differences, in the absorption of radiation along different beams, resulting from differences in the path lengths of the beams through the body; optical means for investigating the position of the attenuating means relative to the body and for providing control signals indicative of said position; and adjusting means for moving said attenuating means in response to said control signals to attain a predetermined position relative to the body.

It is a further object of the invention to provide apparatus, for examining a body by means of penetrating radiation, including: source means for irradiating the body with a fan-shaped distribution of radiation projected in a mean direction; means for scanning the source around the body so as to project the radiation through a cross-sectional slice thereof from a plurality of mean directions; detector means, including a plurality of detectors, for detecting the intensity of the radiation transmitted through the body along a plurality of beams within said distribution at each of said mean directions, and means co-operating with said detectors to provide beam data signals indicative of the absorption suffered by said beams in passing through said body for processing to provide a representative of the distribution of absorption of the radiation in said slice; at least two attenuating masses disposed in the path of said radiation, so that each intercepts substantially all of the beams of radiation incident on the body, to reduce differences in the absorption of the radiation of different beams, resulting from differences in the path lengths of the beams through the body; means for investigating the positions of the attenuating masses relative to the body and for providing control signals indicative of the positions; and adjusting means for adjusting the attenuating masses relative to the body in response to the control signals to attain a predetermined relative position.

It is yet another object of the invention to provide apparatus, for examining a body by means of penetrating radiation, including: source means for irradiating the body with a fan-shaped distribution of radiation projected in a mean direction; means for scanning the source around the body so as to project the radiation through a cross-sectional slice thereof from a plurality of mean directions; detector means, including a plurality of detectors, for detecting the intensity of the radiation transmitted through the body along a plurality of beams within said distribution at each of said mean directions, and means co-operating with said detectors to provide beam data signals indicative of the absorption suffered by said beams in passing through said body for processing to provide a representation of the distribution of absorption of the radiation in said slice; attenuating means disposed in the path of the radiation to reduce differences in the absorption of the radiation along different beams resulting from differences in the path lengths of the beams through the body; optical means for providing control signals indicative of the size of the body; and adjusting means for adjusting the attenuating means in response to said control signals to attain a prescribed degree of reduction of said differences for different sized bodies.

It is another object of the invention to provide apparatus, for examining a body by means of penetrating radiation, including source means arranged to irradiate a cross-sectional slice of the body by a substantially planar distribution of said radiation, means for moving said source in relation to the body to irradiate said slice by radiation projected from a plurality of different directions, detector means arranged to determine the intensity of radiation transmitted through the body along a plurality of beams within said distribution from each of said directions, attenuating means disposed in the path of the radiation to reduce differences in the absorption of the radiation along different beams resulting from differences in path lengths for the radiation through the body, optical means for determining the position of the attenuating means relative to the body and for providing signals indicative of said position and means for moving said attenuating means in response to said signals to attain a prescribed position.

It is another object of the invention to provide apparatus, for examining a body by means of penetrating radiation, including: source means for irradiating the body with a fan-shaped distribution of radiation; detector means comprising a plurality of detectors for detecting the radiation after passage through the body, each detector receiving radiation along a respective beam path and providing a beam data signal representing the absorption of radiation along that path; means for orbiting at least the source about the body to irradiate a section of the body along beam paths at a plurality of angular positions in said section; two attenuating masses each intercepting radiation of substantially all of the beam paths passing through the body to reduce differences, in the absorption of the radiation of different paths, resulting from differences in the path lengths in the body; means for providing control signals indicative of the size of the body; and adjusting means for adjusting the positions of the attenuating masses relative to the body to obtain optimum reduction of said differences for different sizes of body.

It is another object of the invention to provide apparatus, for adjusting the absorption of radiation projected along paths of different length through a body of approximately circular cross-section in a computerised tomographic apparatus, including two attenuating masses each arranged to intercept radiation of substantially all paths passing through the body to reduce differences in the absorption of the radiation resulting from said different path lengths, optical means for providing control signals indicative of the position of the edges of the body and adjusting means responsive to said signals, to adjust the positions of the attenuating masses to attain predetermined positions relative to said edges.

Figure 1B:
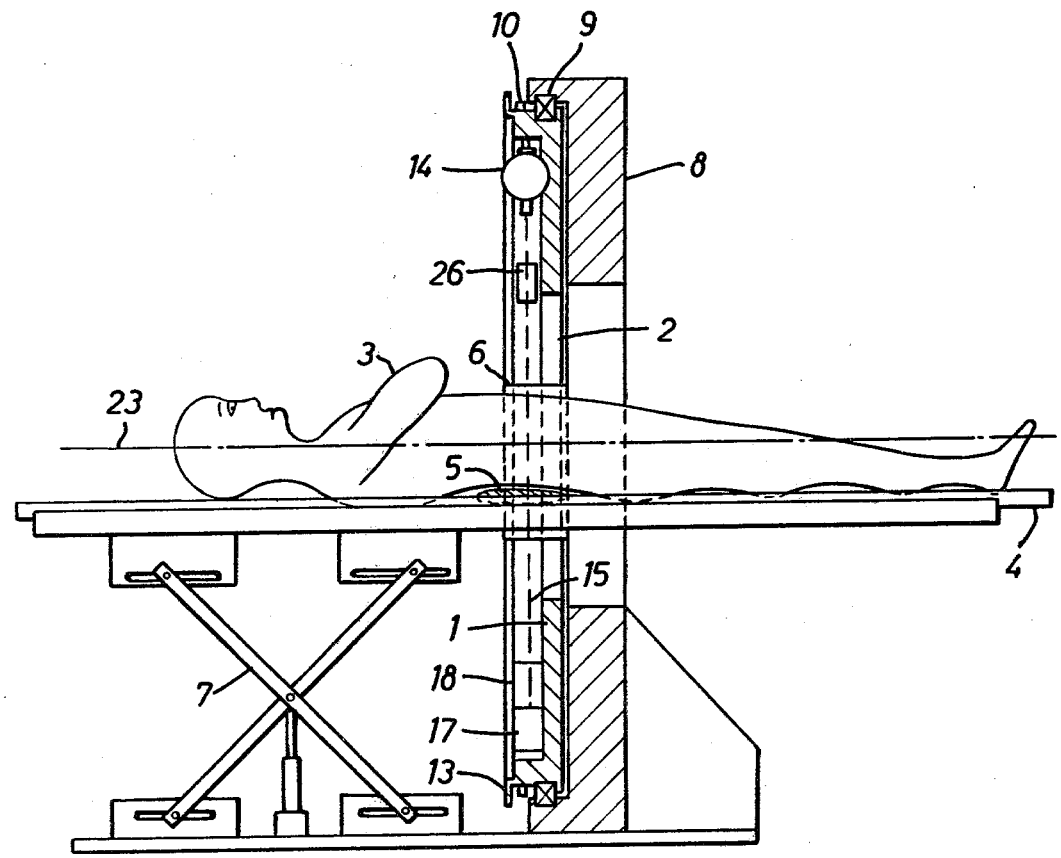
Figure 4A:
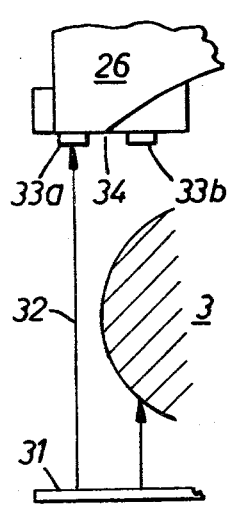
Figure 4B:
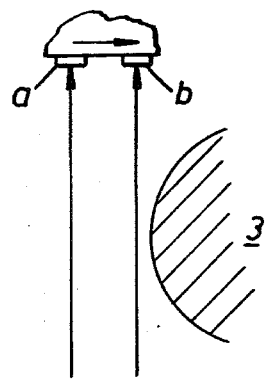
Figure 4C:
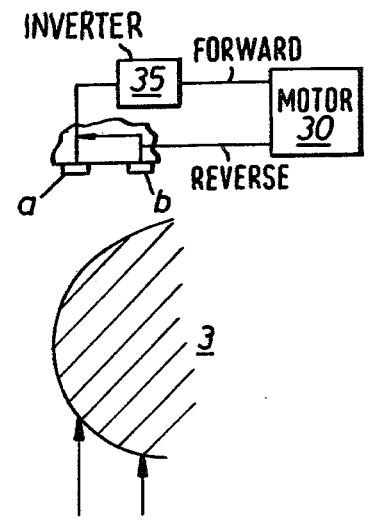
Figure 5:
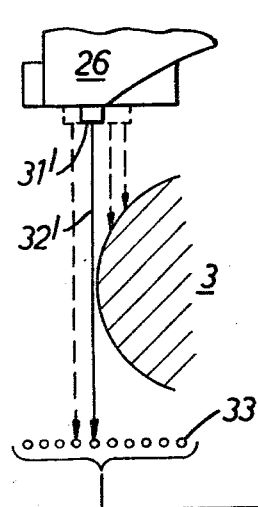
Figure 6:
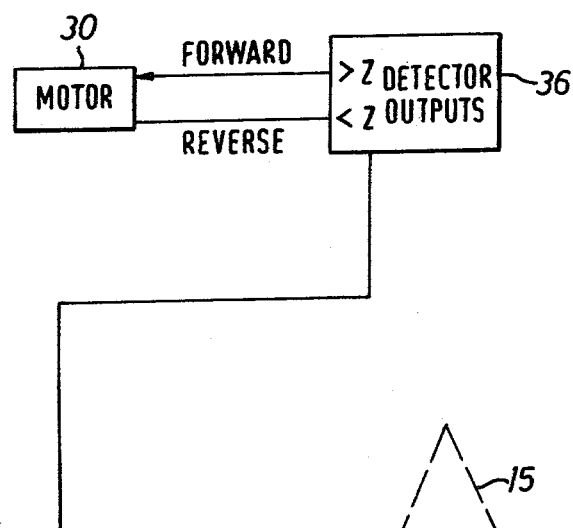
Figure 6:
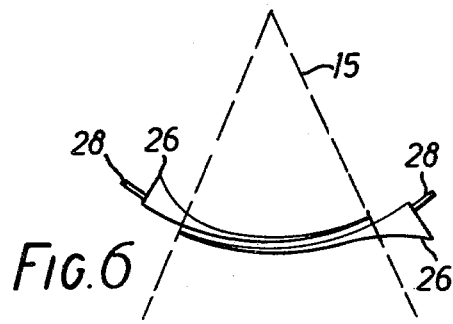

In order that the invention may be clearly understood and readily carried into effect examples thereof will now be described with reference to the accompanying drawings, of which FIGS. 1a and 1b show in end and side elevation respectively an apparatus incorporating the invention, FIGS. 2a and 2b show in end and side elevation respectively, one example of attenuating masses for the invention, FIGS. 3a and 3b show in end and side elevation respectively an alternative arrangement for detecting position of the body edge, FIGS. 4a, 4b and 4c illustrate the operation of the arrangement of FIG. 3, FIG. 5 shows an alternative arrangement to FIG. 3, and FIG. 6 shows a variation of the attenuator arrangement, more especially applicable to rotating fan-beam geometry.

An apparatus with which this invention may be used is shown in end elevation in FIG. 1a and in side elevation in FIG. 1b. It comprises a rotary member 1 which is rotatable about an aperture 2 in which the body 3, of a patient to be examined, can be inserted. The patient is supported on a suitably shaped bed 4. A material 5, having an absorption to the radiation similar to body tissue, is positioned between the body 3 and the bed 4 to substantially exclude air from the gap therebetween and is extended partly about the body to provide an approximately circular cross-section to the radiation. The body is retained firmly in the desired position by means such as a restraining strap 6. Means for supporting and positioning the bed 4 may take any desired form and are indicated generally at 7 as a scissors mechanism operated by a hydraulic actuator.

The rotary member 1 is rotatably mounted on a fixed frame 8, having an aperture at least commensurate with aperture 2, in this example by means of a circular bearing 9. Member 1 is rotated by means of a toothed belt 10 engaging with teeth cut in the periphery of member 1 and driven by a motor 11 fixed to main frame 8.

A light source/photocell device 12, fixed to main frame 8, co-operates with a graticule 13 to provide pulses indicative of the progress of the rotary motion of member 1. Graticule 13 is formed around the entire circumference of member 1 and comprises a transparent substrate having opaque markings formed thereon. By interrupting the light path between light source and photocell these markings provide the desired pulses. Other means of providing suitable pulses may of course be used.

The rotatable member 1 carries a source 14 of a fan-shaped distribution 15 of penetrating radiation, in this example X-rays. The X-rays, which are confined to the fan-shaped distribution by collimator means 16 are, after passage through the body 3, incident on a detector means 17. The detector means comprises a plurality of individual detectors lying in the plane of the slice to be examined such that each detector receives radiation transmitted through body 1 along a respective one of a plurality of narrow beams of radiation distributed at different angular dispositions within the fan 15. The detectors, which in a typical embodiment number 120, can be of any suitable type, for example scintillation crystals with associated phomultipliers or photodiodes. A bank of collimators 18 is also provided to reduce the incidence on the detectors of radiation scattered in the body 3. Furthermore collimator means 16 may be arranged to divide the radiation into beams corresponding to respective detectors, to reduce the incidence of unnecessarily intense radiation on the patient.

Although in this example the source 14 is fixed in relation to the detectors 17, it should be noted that the arrangement may be one in which the radiation is moved relative to the detectors. This may be by the use of an X-ray tube of the type in which the point source of the radiation can be scanned across the surface of the tube anode; the operation being, for example, as described in U.S. Pat. No. 4,010,370.

In operation the source 14 irradiates the body 3 with the fan 15 of X-rays. The X-rays are partially absorbed by the body and the intensity, after such absorption, is measured by detectors 17. The output of each detector is applied to a respective channel, of which only one is shown in the drawing. Each channel comprises, in series, an amplifier such as 19, an integrator such as 20, an analogue-to-digital converter (ADC) such as 21 and a logarithmic converter such as 22. In the course of examination the rotatable member 1 is rotated about axis 23 to orbit the source 14, and therefore fan 15 of radiation, and detectors 17 about body 3. Each integrator such as 20 integrates the signal in its channel for a period representing a predetermined degree of rotational motion. It thus provides an analogue signal representing the total intensity of radiation incident on the respective detector in that time and transmitted through the body 3 along a path effectively examined by that detector taking into account the rotational motion. Information about the progress of the rotation is provided by the pulses from light source and photocell unit 12 and these pulses are used to set and reset the integrators at the desired intervals to provide the said analogue signals.

One or more of units 19–22 may be provided on member 1 in the vicinity of detectors 17. At a suitable stage the signals being provided are transmitted, by means not shown such as slip rings or looped cables, to be applied, together with similar signals or other channels, to a processing unit 24. Unit 24 processes the digital signals from all of the detectors to provide the desired representation of a cross-sectional slice of the body 3. The processing may be of any suitable type such as that described in U.S. Pat. No. 3,778,614 or the convolution technique described in U.S. Pat. No. 3,924,129. In the case of the latter technique the data may be reordered into sets representing sets of parallel radiation paths through the body. The convolution may, however, in appropriate form be applied to data for the fan distribution of paths for which they are acquired. The processed data are then applied to a display unit 25, which may be a television monitor, or held in storage, not shown.

It will be apparent that all path lengths of the radiation through body 3 are not equal in view of the approximately circular cross-section of the body and the surrounding material. For this reason the outer detectors of the array tend to give higher outputs than centrally disposed detectors, even for a body of uniform absorption. This may be mitigated by appropriately adjusting the gains of the respective detectors and/or amplifiers or by correction in processing. However such correction allows the body to be subject to unnecessary radiation. It has therefore been the practice to insert suitably shaped bodies to provide attenuating masses between source 14 and body 3, or between body 3 and detectors 17 or both, to substantially equalise the path lengths.

The arrangement described so far is essentially that described in U.S. Pat. No. 3,881,110 or U.S. Pat. No. 3,937,963. The use of attenuating bodies to equalise absorbing paths is, however, more fully described in U.S. Pat. No. 3,946,234.

It has been the practice to change the attenuating bodies when examining patients of different sizes so that those used give the best correction for the patient being examined and minimise the discontinuity in absorption which can occur at the edge of the attenuating body if incorrectly sized attenuators are adjusted. This invention provides adjustable wedge-shaped attenuating bodies, shown at 26 in FIG. 1, which can be automatically adjusted to suit different sizes of patient.

The arrangement of the wedge-shaped bodies 26 is shown in greater detail in FIGS. 2a and 2b. Each wedge 26 is relatively large at one end and then of decreasing thickness with length and has a relatively thin part 26' of sufficient length to extend across the entire fan of radiation. Each wedge 26 runs on bearings 27 in tracks 28 in rotary member 1. A lead screw 29, driven by a motor such as 30 also fixed to member 1, serves to drive each wedge in one or the other direction along its respective track 28. On one side of the body 3 there is mounted a strip which is a source 31 of parallel light 32. This may be a conventional strip light with suitable lenses and collimators. On the other side there is mounted a plurality of light detectors, such as photodiodes 33, in this example grouped in two sets. As can be seen from FIG. 2, the outputs of detectors 33 indicate the extent of the shadow cast, in the parallel light 32, by body 3. The motors 30 are then servoed to the detector outputs, so driving wedges 26 together or apart until they present a combined attenuation to the radiation which has been predetermined to be suitable for a body 3 of that size. Although light source 31 and detectors 33 may be placed in any suitable position, it is desirable to place them so as to be as close as possible to the radiation 15, without obstructing it. A suitable arrangement is shown in FIG. 2b. They can alternatively be arranged to be in the radiation path but be moved out before examination proceeds.

It will be seen that the extensions of the wedges 26 to parts 26' are sufficient to ensure that each wedge 26 extends right across the fan of radiation 15 throughout the range of adjustment. This assumes that the radiation incident on the body 3 does not include a discontinuity in the intensity distribution such as would result from the two shorter wedges moved towards and away from each other.

In an alternative embodiment of the invention, illustrated in FIGS. 3a and 3b, two detectors 33 are mounted on each of the wedges 26 and the light source 31 on the other side of body 3. The wedges 26 are dimensioned so that a predetermined point 34 should overlie the edge of body 3 for satisfactory adjustment and one detector 33 is positioned on each side of that point. The motors 30 then move their respective wedges until one detector 33 is illuminated and the other is not.

The operation can be seen more clearly in FIG. 4. In FIG. 4a a detector 33a is illuminated while detector 33b is shaded by body 3. The wedge 26 is therefore satisfactorily adjusted. In FIG. 4b both detectors are illuminated. As a result motor 30 is caused to move wedge 26 to the right until the output from 33b ceases. In FIG. 4c neither are illuminated and motor 30 is caused to move wedge 26 to the left until an output is obtained from 33a. The desired effect is obtained as shown in FIG. 4c by applying the output of detector 33a, via an inverter 35, to one control of motor 30, designated 'forward,' and the output of detector 33b directly to the other control designated 'reverse.' A similar pair of detectors 33 co-operate with the other motor 30 to adjust the other wedge 26 in the same manner.

In a further embodiment of the invention a variety of the arrangement of FIG. 4 may be implemented using the stationary array of detectors 33 of FIG. 2. This arrangement, illustrated in FIG. 5, employs at least one source 31', of a narrow beam of light 32', mounted on each wedge 26. The beam 32' is arranged perhaps, to illuminate one detector 33 and the wedge is moved until no detectors are illuminated. Preferably the beam can be arranged, as shown by the broken lines in FIG. 5, to illuminate a larger number, say four, detectors. The wedge can then be moved, by motor 30 in response to logic circuits 36, until only some detectors are illuminated, say two. Thus correction can be made for excessive movement, since if less than two detectors are illuminated the wedge can be moved in the reverse direction until the required two outputs are obtained.

The invention has been described in terms of an apparatus employing simple rotation of a fan of X-rays and a co-operating detector array. In this case it may be desirable to provide means for correcting for or evaluating drift in the sensitivities of individual detectors during the examination. The invention may, however, be used with any radiographic apparatus in which the problem, of adjusting radiation intensity to the body profile, arises. This includes specific arrangements mentioned hereinbefore, incorporating motion of the radiation source relative to the, perhaps stationary, detectors, and arrangements using a combined rotational and translational motion of the radiation source. For such embodiment problems of detector drift may be more readily overcome.

The arrangement of wedges 26, with their facing surfaces being straight and perpendicular to the centre line of the radiation, is particularly suitable to arrangements including a translational motion. The translational motion is then usually parallel to those facing surfaces. The arrangement does, however, as described provide a satisfactory result for a purely rotational fan beam geometry. If it is desired a modified arrangement may be used which is more especially designed for the rotational fan beam geometry. Such an arrangement is shown in FIG. 6. The wedges 26 are of essentially the same form as described hereinbefore but the facing surfaces, while still parallel, are curved so that they are perpendicular to all of the beams in the fan 15 of radiation. The tracks 28, in which wedges 26 move, are similarly curved, other arrangements being essentially the same. This curved form allows more freedom, to those implementing a particular installation of the invention, to cause both wedges to act substantially equally although one wedge lies in a more convergent part of the beam than the other.

Other embodiments of the invention, in particular other positions of the light source and detectors, will be apparent to those skilled in the art.

What I claim is:

1. Apparatus, for examining a body by means of penetrating radiation, including: source means for irradiating the body with a fan-shaped distribution of radiation projected in a mean direction, means for scanning the source around the body so as to project the radiation through a cross-sectional slice thereof from a plurality of mean directions; detector means, including a plurality of detectors, for detecting the intensity of radiation transmitted through the body along a plurality of beams within said distribution at each of said mean directions, and means cooperating with said detectors to provide beam data signals indicative of the absorption suffered by said beams in passing through said body for processing to provide a representation of the distribution of absorption of the radiation in said slice; attenuating means, disposed in the path of the radiation, for reducing differences, in the absorption of radiation along different beams, resulting from differences in the path lengths of the beam through the body; optical means for investigating the position of the attenuating means relative to the body and for providing control signals indicative of said position; and adjusting means for moving said attenuating means in response to said control signals to attain a predetermined position relative to the body.

2. An apparatus according to claim 1 wherein the attenuating means comprises two attenuating masses each capable of independent movement relative to the body.

3. An apparatus according to claim 2 wherein each of the attenuating masses is substantially wedge-shaped.

4. An apparatus according to claim 2 wherein each of the attenuating masses is of sufficient extent to intercept substantially all of the radiation beams incident on the body.

5. An apparatus according to claim 1 wherein the optical means comprises at least one source of light situated on one side of the body and a plurality of light detectors situated on the other side of the body for determining interception of the light by the body.

6. An apparatus according to claim 5 wherein the source of light is a source of parallel light.

7. An apparatus according to claim 5 wherein the attenuating means comprises two attenuating masses, and some of the light detectors are situated on each of said masses.

8. An apparatus according to claim 7 wherein the adjusting means includes means for moving one of said attenuating masses such that at least one of the light detectors situated thereon is illuminated by the light source and at least one is shielded therefrom by the body.

9. An apparatus according to claim 8 wherein the said one of said attenuating masses has two light detectors situated thereon.

10. An apparatus according to claim 5 wherein the attenuating means comprises two attenuating masses and at least one light source is mounted on each of said masses.

11. An apparatus according to claim 10 including means for moving one of said attenuating masses until a predetermined number of said light detectors are illuminated.

12. Apparatus, for examining a body by means of penetrating radiation, including: source means for irradiating the body with a fan-shaped distribution of radiation projected in a mean direction; means for scanning the source around the body so as to project the radiation through a cross-sectional slice thereof from a plurality of mean directions; detector means, including a plurality of detectors, for detecting the intensity of the radiation transmitted through the body along a plurality of beams within said distribution at each of said mean directions, and means cooperating with said detectors to provide beam data signals indicative of the absorption suffered by said beams in passing through said body for processing to provide a representation of the distribution of absorption of the radiation in said slice; at least two attenuating masses disposed in the path of said radiation so that each intercepts substantially all of the beams of radiation incident on the body, to reduce differences in the absorption of the radiation of different beams, resulting from differences in the path lengths of the beams through the body; means for investigating the positions of the attenuating masses relative to the body and for providing control signals indicative of the positions; and adjusting means for adjusting the attenuating masses relative to the body in response to the control signals to attain a predetermined relative position.

13. Apparatus, for examining a body by means of penetrating radiation, including: source means for irradiating the body with a fan-shaped distribution of radiation projected in a mean direction; means for scanning the source around the body so as to project the radiation through a cross-sectional slice thereof from a plurality of mean directions; detector means, including a plurality of detectors for detecting the intensity of the radiation transmitted through the body along a plurality of beams within said distribution at each of said mean directions, and means cooperating with said detectors to provide beam data signals indicative of the absorption suffered by said beams in passing through said body for processing to provide a representation of the distribution of absorption of the radiation in said slice; attenuating means disposed in the path of the radiation to reduce differences in the absorption of the radiation along different beams, resulting from differences in the path lengths of the beams through the body; optical means for providing control signals indicative of the size of the body; and adjusting means for adjusting the attenuating means in response to said control signals to attain a prescribed degree of reduction of said differences for different sized bodies.

14. An apparatus according to claim 13 in which the attenuating means comprises two attenuating masses each capable of independent movement relative to the body and each of sufficient extent to intercept substantially all of the radiation beams incident on the body and in which the adjusting means includes means for moving the attenuating masses relative to the body.

15. Apparatus, for examining a body by means of penetrating radiation, including source means arranged to irradiate a cross-sectional slice of the body by a substantially planar distribution of said radiation, means for moving said source in relation to the body to irradiate said slice by radiation projected from a plurality of different directions, detector means arranged to determine the intensity of radiation transmitted through the body along a plurality of beams within said distribution from each of said directions, attenuating means disposed in the path of the radiation to reduce differences in the absorption of the radiation along different beams resulting from differences in path lengths for the radiation through the body, optical means for determining the position of the attenuating means relative to the body and for providing signals indicative of said position and means for moving said attenuating means in response to said signals to attain a prescribed position.

16. Apparatus, for examining a body by means of penetrating radiation including: source means for irradiating the body with a fan-shaped distribution of radiation; detector means comprising a plurality of detectors for detecting the radiation after passage through the body, each detector receiving radiation along a respective beam path and providing a beam data signal representing the absorption of radiation along that path; means for orbiting at least the source about the body to irradiate a section of the body along beam paths at a plurality of angular positions in said section; two attenuating masses each intercepting radiation of substantially all of the beam paths passing through the body to reduce differences, in the absorption of the radiation of different paths, resulting from differences in the path lengths in the body; means for providing control signals indicative of the size of the body; and adjusting means for adjusting the positions of the attenuating masses relative to the body to obtain optimum reduction of said differences for different sizes of body.

17. Apparatus according to claim 16 in which the means for providing control signals comprises at least one source of light on one side of the body and a plurality of detectors arranged on the other side of the body to intercept said light.

18. Apparatus, for adjusting the absorption of radiation projected along paths of different lengths through a body of approximately circular cross-section in a computerised tomographic apparatus, including two attenuating masses each arranged to intercept radiation of substantially all paths passing through the body to reduce differences in the absorption of the radiation resulting from said different path lengths, optical means for providing control signals indicative of the position of the edges of the body and adjusting means responsive to said signals to adjust the positions of the attenuating masses to attain predetermined positions relative to said edges.

* * * * *